(12) United States Patent
Asiri et al.

(10) Patent No.: US 9,538,924 B1
(45) Date of Patent: Jan. 10, 2017

(54) COMPOSITION AND METHOD OF MAKING A STRAIN SENSOR AND ITS USE

(71) Applicant: KING ABDULAZIZ UNIVERSITY, Jeddah (SA)

(72) Inventors: Abdullah Mohamed Asiri, Jeddah (SA); Sher Bahadar Khan, Jeddah (SA); Muhammad Tariq Saeed Chani, Dushanbe (TJ); Khasan S Karimov, Dushanbe (TJ)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 14/860,897

(22) Filed: Sep. 22, 2015

(51) Int. Cl.
*A61B 5/02* (2006.01)
*A61B 5/024* (2006.01)

(52) U.S. Cl.
CPC .... *A61B 5/02444* (2013.01); *A61B 2562/0261* (2013.01); *A61B 2562/0285* (2013.01); *A61B 2562/12* (2013.01)

(58) Field of Classification Search
CPC ............ A61B 5/02444; A61B 2562/12; A61B 2562/0261; A61B 2562/0285
See application file for complete search history.

*Primary Examiner* — Paula J Stice
(74) *Attorney, Agent, or Firm* — Greta Kadambi; Riddhi IP LLC

(57) ABSTRACT

A strain sensor fabrication and its use as flexible elastic heart strain sensors in form of a Wheatstone bridge are described. All arms of the bridge are nanocomposite based strain sensors. The silver selenide nanocomposite is especially developed by simple rubbing in method where the nanomaterials such as carbon nanotubes (CNTs) and $Ag_2Se$ nanoparticles are embedded into a porous rubber. This is a low cost easy to make strain sensor that has excellent resistance to humidity and temperature.

5 Claims, 7 Drawing Sheets

COMPOSITION AND METHOD OF MAKING A STRAIN SENSOR AND ITS USE

FIELD OF TECHNOLOGY

This disclosure generally relates to composition and method of making a strain sensor and using it as a heart rate strain sensor. More specifically fabrication of elastic heart rate strain sensor as a Wheatstone bridge is described.

BACKGROUND

The wearable market is exploding and the heart rate monitors and other measuring devices are becoming increasingly important. Many individuals are becoming more conscious of their health and many others are suffering from heart diseases. To aid these individuals and patients a cardiac pacemaker is surgically placed in the body. Pacemakers have a problem of occasional failure or premature discharging of the batteries. In hospitals there are testing devices for the monitoring of heart rate. However, usually these devices are quite bulky. The real problem associated with these essentially stationary testing devices is that they are intrusive and are not adapted to be worn by the patient outside of the hospital. Therefore a number of heart rate sensors were designed and fabricated that was based on different physical principles. Out of these the simplest and reliable sensors are based on strain sensors.

For heart rate measurements a finger-mounted strain sensor for the measurement of small volume of blood changes can be used (Aston R., et al 1991). A strain sensor is a device that converts the changes in the length ($\Delta l$) of the sensor or object into change in the resistance ($\Delta R$) in the sensor. Strain (S) is ratio of $\Delta l$ to length (l):

$$S = \Delta l / l \quad (1)$$

Sensitivity of sensor or gauge factor (G) is:

$$G = \Delta R / RS \quad (2)$$

The strain sensitivities of some sensors that are used in practice, for example, for constantan and silicon are equal to 2.1 and 120, respectively. Cardiac monitor that can be strapped around the wrist (where a radial pulse is normally detected) was developed (Manual B et. al., U.S. Pat. No. 3,742,937). The sensor can detect heart rate and abnormalities in the heart beat rate.

Broadwater et. al (1982) fabricated a digital watch for the measurement of systolic and diastolic blood pressure and heart rate. This watch has a piezoelectric transducer that is held in contact with the wrist adjacent to the radial artery. The electronic circuitry of the watch allows to detect blood pressure pulses and systolic and diastolic pressures.

Pinter and Muehlsteff (2009) have developed a sensor for the combined heart rate and respiration measurement of a patient. The sensor consists of a strain gauge that is assembled on an elastic carrier and two stickers for sticking the sensor on the patient's chest. The movements of the patient's chest due to heart beat and/or respiration lead to a varying strain gauge signals.

Rytky (US 2006/0142654 A1) fabricated a sensor system, a garment and a heart rate monitor. The sensor system comprises at least one flexible film structure consisting of a first insulation layer, at least one electric conductor layer formed on the top of first insulation layer and an electrode area, which is configured to establish an electric contact with the surface of the user's skin and to generate an output signal (electric signals) proportional to a momentary value of the electrocardiogram.

The invention by Sullivan (U.S. Pat. No. 7,689,271) determines the heart rate and respiration rate of a patient through the patient's extremities. Heart rate and respiration rate are determined via an energy spectrum, period gram or histogram using a time series analysis. A patient can stand near the device and lean on it, or stand on a piezoelectric pad. A microcomputer provides calculations to determine heart and respiratory rates using signal processing and time series analysis of data. For heart rate measurements, a finger-mounted or strapped about the wrist strain sensor (which measures small changes in the volume of blood) can be used. The strain sensor is usually connected in one of the arms of Wheatstone bridge. Sensitivity, reliability, cost and size of the strain sensors depends on materials, technology of fabrication and sensor circuit. This circuit connects the sensor or sensors to electronic circuit that filters, amplifies counts (heart pulse rates) and displays them on the screen. However, there is a need for a better composite that is cost effective, accurate and sensitive.

SUMMARY

The invention discloses the composition and method of making the strain sensor and using the same as a heart rate sensor in form of a Wheatstone bridge in several devices. In one embodiment, a composition of a strain sensor is described.

In another embodiment, a multiwall carbon nanotube powder having a diameter between 10-30 nm; a spherical silver selenide nanoparticle of a specific size at 50% wt is added to 50% wt of a carbon nanotube powder; and a porous rubber having a specific length, width and thickness was mixed with the carbon nanotube powder and the spherical silver selenide nanoparticle to make a rubber-CNT-silver selenide complex to be used to make a Wheatstone bridge that would be used as the strain sensor having a specific length, width and thickness.

In another embodiment, the specific length, width and thickness of the porous rubber is 50 mm*20 mm*5 mm. In another embodiment, wherein the specific length, width and thickness of the Wheatstone bridge is 20 mm*10 mm*1 mm. In one embodiment, the specific size for the spherical silver selenide nanoparticle is between 0.001 to 100 nm. In another embodiment, the spherical silver selenide nanoparticle is made by combining a silver nitrate solution and sodium selenide solution in a 2:1 ratio.

In one embodiment a method of making or fabricating the strain sensor is described. In one embodiment, adding a specific volume and concentration of sodium selenide and a specific volume and a specific concentration of silver nitrate to make a silver selenide solution; stirring the silver selenide solution overnight and heating it at 60° C.; washing the stirred and heated silver selenide solution and calcinate at 500° C. for three hours to obtain a spherical silver selenide nanoparticle of specific size; mixing the spherical silver selenide nanoparticle and a carbon nanotube of a specific size at a specific ratio to form a nanocomposite; and mixing the nanocomposite with a porous rubber to make a strain sensor as a Wheatstone Bridge is described. In another embodiment, making a four arm Wheatstone bridge and passing a current to see the resistance and relaxation of the four arms to show the function of the heart is described. In another embodiment, the silver selenide solution is made by combining a silver nitrate solution and sodium selenide solution in a 2:1 ratio. In another embodiment, the specific volume and concentration of the sodium selenide is 50 ml and 0.1M. In another embodiment, the specific volume and concentration of the silver nitrate is 50 ml and 0.2M respectively.

In one embodiment, all arms of the bridge are nanocomposite based strain sensors. In another embodiment, all the arms of the Wheatstone bridge is balanced. In another embodiment, the nanocomposite is especially developed by simple rubbing in or mixing method where the nanomaterials such as carbon nanotubes (CNTs) and spherical silver selenide nanoparticle ($Ag_2Se$) are embedded into a porous rubber.

In one embodiment, fabrication of flexible elastic strain Wheatstone bridge sensors based on nanomaterials and porous rubber composite for biomedical applications, in particular, for heart rate measurement.

In one embodiment, method of making and/or fabrication of flexible elastic strains Wheatstone bridge sensors based on nanomaterials and porous rubber composite by use of carbon nanotubes (CNT)-porous rubber composite and CNT-$Ag_2Se$-porous rubber composite the sensors are fabricated by rubbing in of the carbon nanotubes (CNT) or the blend of 50 wt. % CNT and $Ag_2Se$ to the porous rubber for making of composite.

In one embodiment, method of making or fabrication of flexible elastic strain Wheatstone bridge sensors based on nanomaterials and porous rubber composite of claim 1 wherein the balancing of the Wheatstone bridge sensors at unloaded condition is made by rubbing in the carbon nanotubes (CNT) or blend of 50 wt. % CNT and $Ag_2Se$ in to the porous rubber. In another embodiment, method of making or fabrication of flexible elastic strain Wheatstone bridge sensors based on nanomaterials and porous rubber composite of claim 1 wherein the composite (CNT, $Ag_2Se$ and porous rubber) developed with low temperature coefficient of resistivity.

In another embodiment, fabrication of flexible elastic strain Wheatstone bridge sensors based on nanomaterials and porous rubber composite of claim 1 wherein the developed composite (CNT, $Ag_2Se$ and porous rubber) has less sensitive to humidity.

In one embodiment, fabrication of flexible elastic strain Wheatstone bridge sensors based on nanomaterials and porous rubber composite of claim 1 wherein the change in composition of the composite (CNT and $Ag_2Se$ in porous rubber) allows to change the initial resistances of the strain sensors in the arms of the Wheatstone bridge.

The novel strain sensor composition, method of making and method of using the novel strain sensor as a heart rate sensor, disclosed herein, may be implemented in any means for achieving various aspects. Other features will be apparent from the accompanying figures and from the detailed description that follows.

BRIEF DESCRIPTION OF THE DRAWINGS

Example embodiments are illustrated by way of example and no limitation in the tables and in the accompanying figures, like references indicate similar elements and in which.

Other features of the present embodiments will be apparent from the accompanying figures and the detailed description that follows.

DETAILED DESCRIPTION

Several embodiments for a method of making and/or fabricating flexible elastic strain sensor, having a specific composition, to be used as a heart rate sensor in form of a Wheatstone bridge are disclosed. Although the present embodiments have been described with reference to specific example embodiments, it will be evident that various modifications and changes may be made to these embodiments without departing from the broader spirit and scope of the various embodiments.

Figure 1B:
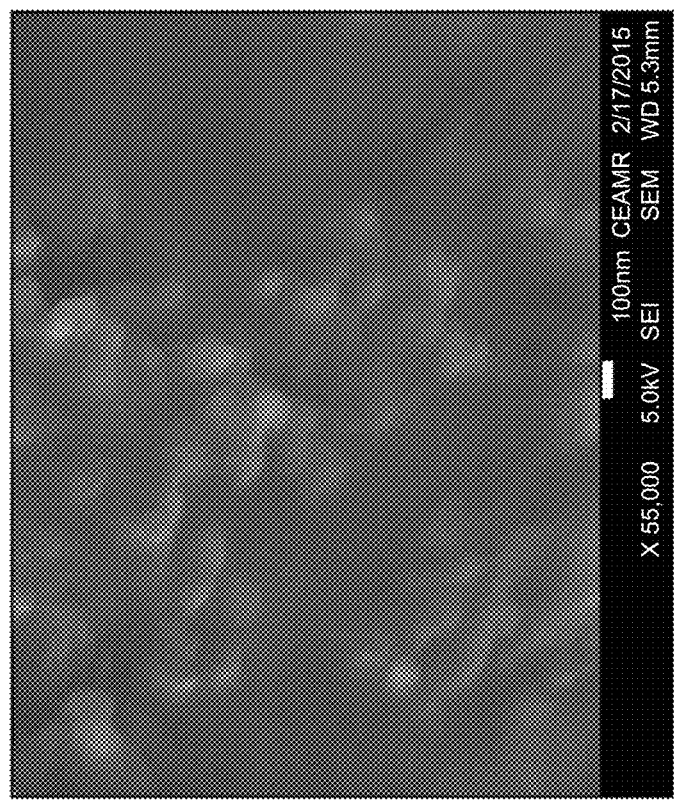
FIGS. 1 (a) and 1(b) shows Field emission scanning electron microscope (FESEM) images of $Ag_2Se$ grown in the form of spherical particle with particle size of less than 100 nm.
Figure 1A:
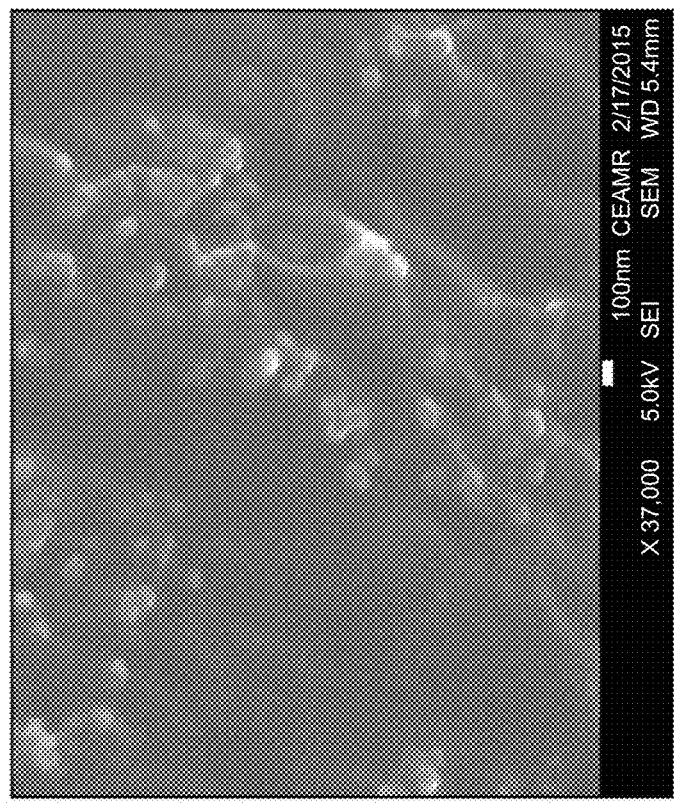
Figure 2:
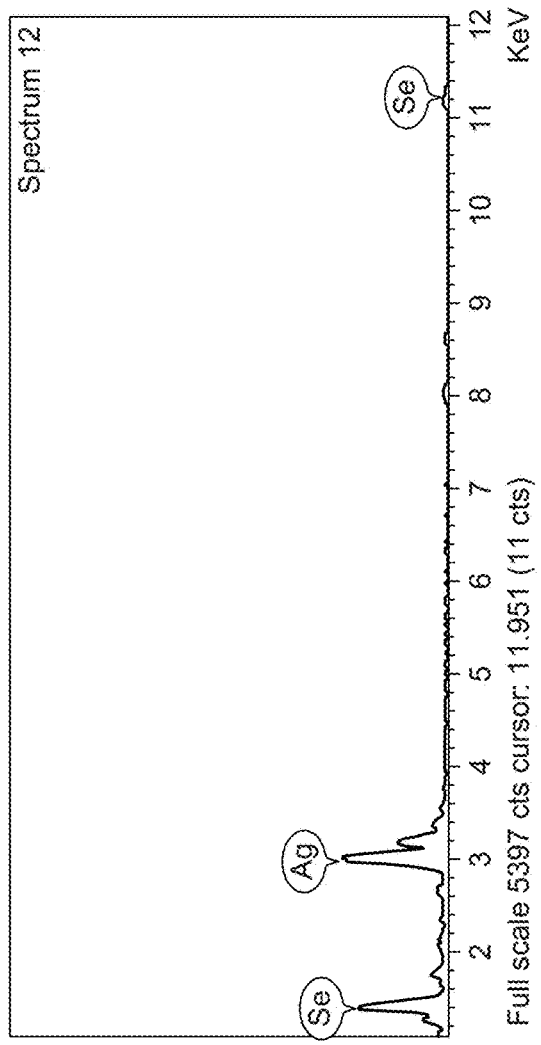
FIG. 2 shows Energy dispersive X-rays spectrometry (EDS) oxford-EDS system which indicates peak for Selenium (Se) and Silver (Ag).

The commercially available (Sun Nanotech Co Ltd., China) multiwall CNTs powder with diameter varied between 10-30 nm was used in the experiments. Silver selenite ($Ag_2Se$) nanoparticles in spherical form were synthesized by simple low temperature method. In the typical procedure, 50 ml of 0.1 M aqueous solution of Sodium selenite ($Na_2Se$) solution was added to 50 ml (specific volume) of 0.2 M (specific concentration) aqueous solution of silver nitrate. The mixture was stirred overnight at room temperature and heated to 60° C. The resulting product was washed and further calcined at 500° C. for three hours. The morphology of spherical $Ag_2Se$ nanoparticles was characterized by using field emission scanning electron microscope (FESEM), JEOL (JSM-7600F, Japan). FESEM images (FIGS. 1(a) and 1 (b)) shows that $Ag_2Se$ nanoparticles are grown in the form of spherical particle with particle size of less than 100 nm. Elemental analysis of spherical $Ag_2Se$ nanoparticle was carried out by energy dispersive X-rays spectrometry (EDS) oxford-EDS system which indicates peak for Se and Ag (FIG. 2). Thus EDS identifies the presence of selenium and silver with the weight % compositions of 1:2. Thus the EDS data reflect that the nanoparticles were made of $Ag_2Se$.

Figure 3A:
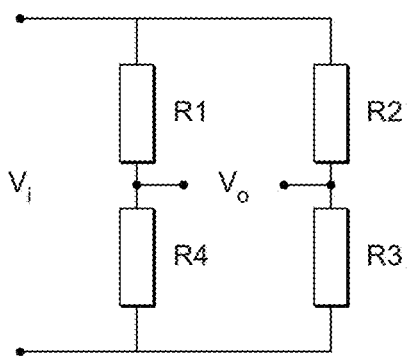
FIG. 3(a), FIG. 3(b) and FIG. 3(c) show schematic diagrams of electric circuit of Wheatstone bridge, square and rectangular shape Wheatstone bridge strain sensors.
Figure 3B:
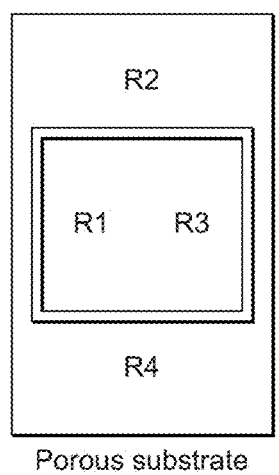
Figure 3C:
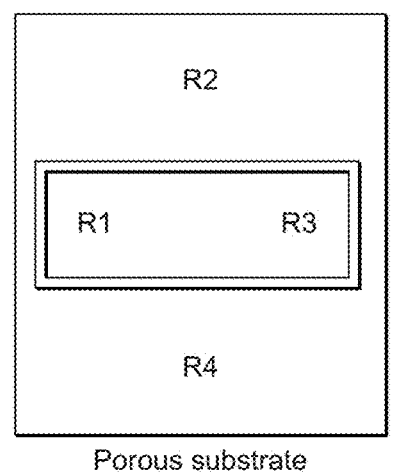
Figure 4A:
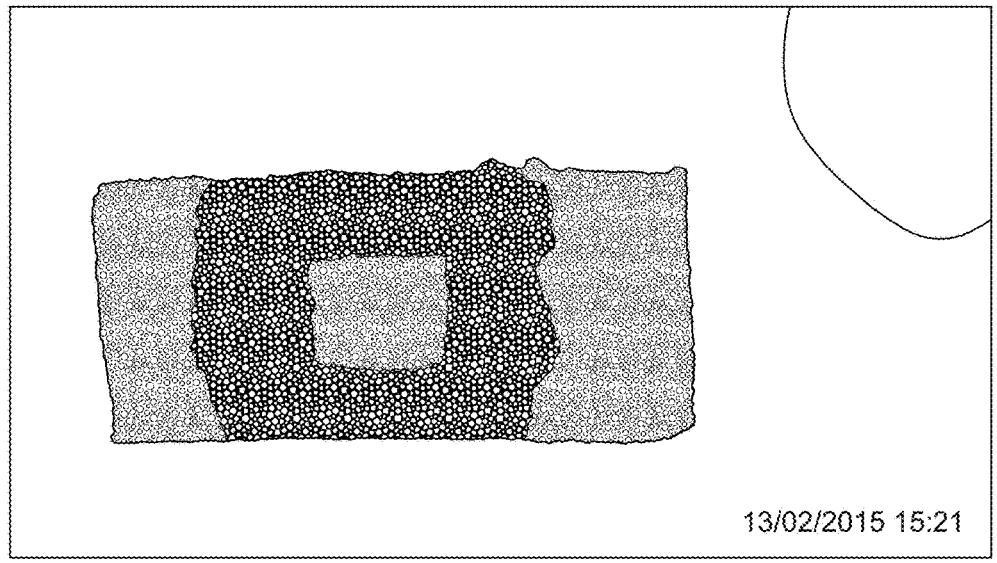
FIG. 4(a) and FIG. 4(b) show photographs of the Wheatstone bridge strain sensors.
Figure 4B:
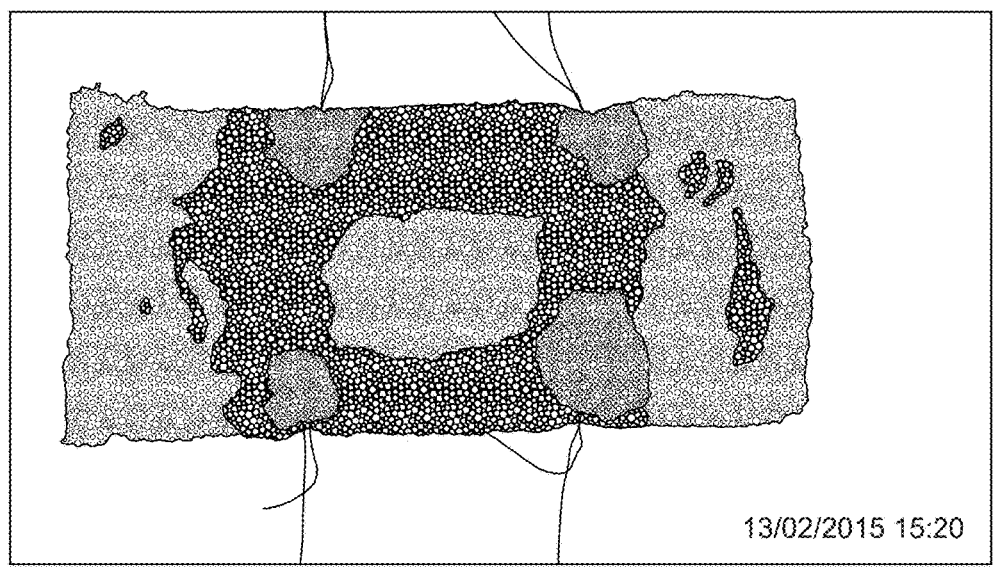
Figure 5:
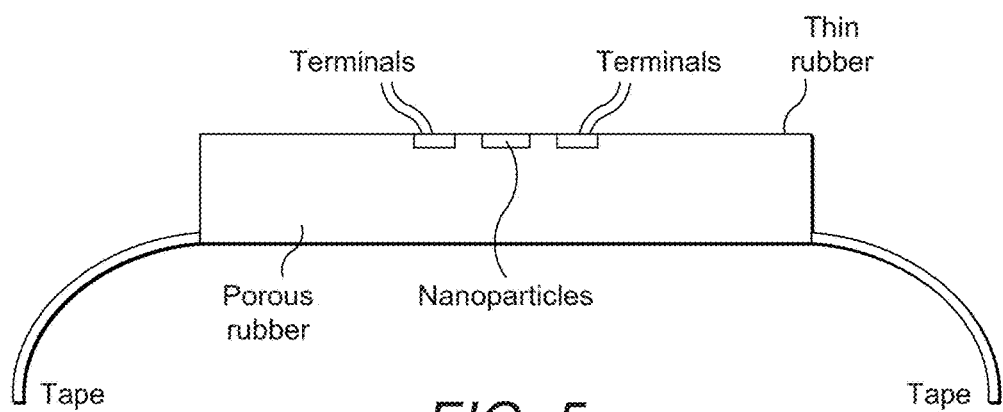
FIG. 5 shows the schematic diagram of the assembled Wheatstone bridge strain sensor (side view).

Carbon nano-tubes (CNTs) powder is blended with 50% wt. spherical $Ag_2Se$ nanoparticle were used for the fabrication of nanocomposites with porous rubber in order to fabricate strain sensors accommodated as Wheatstone bridge. Optical microscope images of porous rubber, porous rubber-CNT and porous rubber-CNT-$Ag_2Se$ showed that the sizes of the pores of rubber substrate were mostly in the range of 20-200 μm. FIGS. 3(a-c) show schematic diagrams of electric circuit of Wheatstone bridge, square and rectangular shape Wheatstone bridge strain sensors, respectively fabricated by rubbing in technology of nanomaterials. Every sides of the square and rectangular shown in FIGS. 3(b) and 3(c) is equal to the concerned resistances of the electric circuit of the Wheatstone bridge shown in FIG. 3(a). Rubbing in (or mixing in) technology is simple and cheap. FIG. 4(a) and FIG. 4(b) show photos of the Wheatstone bridge strain sensors. In FIG. 4(a) is shown only Wheatstone bridge without of connecting wires, in FIG. 4(b) is shown Wheatstone bridge with connecting wires. The wires are connected with Wheatstone bridge by use of silver paste. The size of porous rubber substrate was 50 mm×20 mm×5 mm, while the sensors length, width and thickness in the Wheatstone bridge were equal to 20 mm, 10 mm and 1 mm, respectively. FIG. 5 shows the schematic diagram of the assembled Wheatstone bridge strain sensor (side view). The strain sensors are flexible and elastic. By tapes shown in FIG. 5 the strain sensor is fixed on the finger or hand of patient. The dependence of the resistance and strain on stress was investigated by using laboratory equipment fabricated for this purpose. For the measurement of resistance the LCR meter MT 4090 was used.

Figure 6A:
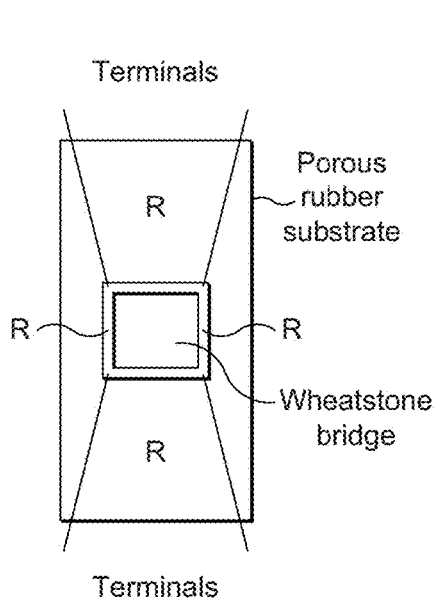
FIG. 6 (a) and FIG. 6 (b) show the schematic diagrams of the constant voltage Wheatstone bridge strain sensors without load and with load.
Figure 6B:
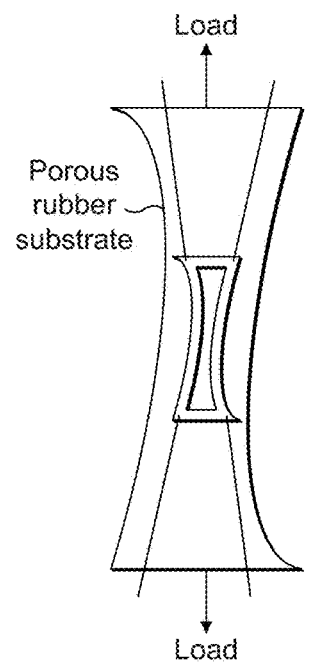
Figure 7:
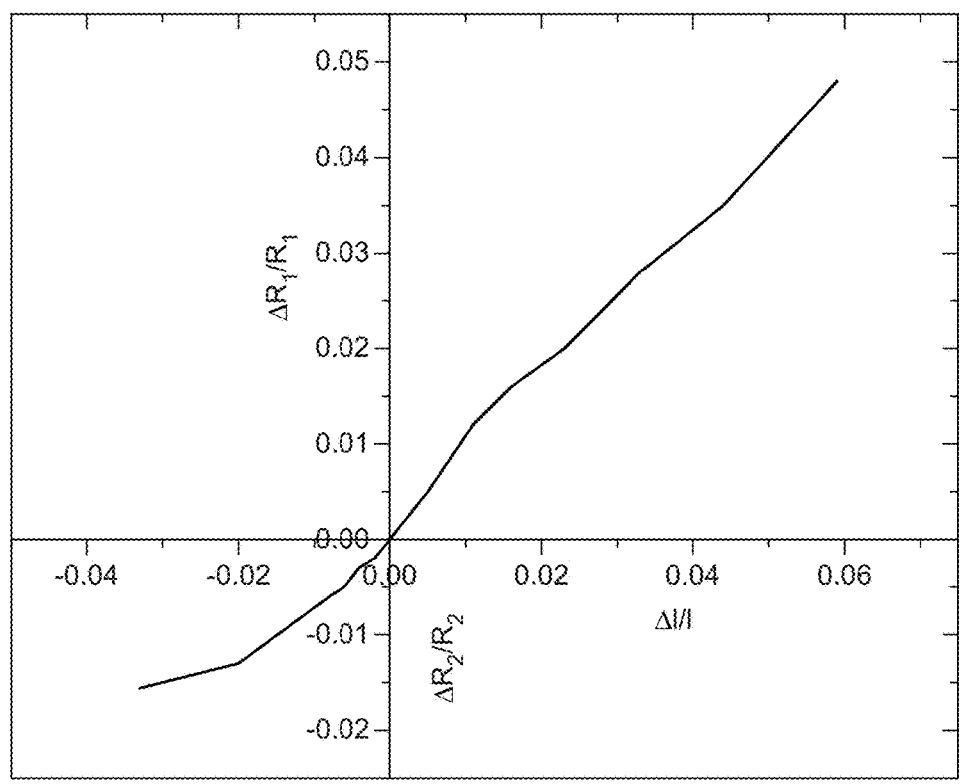
FIG. 7 shows $\Delta R_1/R_1$ and $\Delta R_2/R_2$ relationships with strain ($\Delta l/l$).
Figure 8:
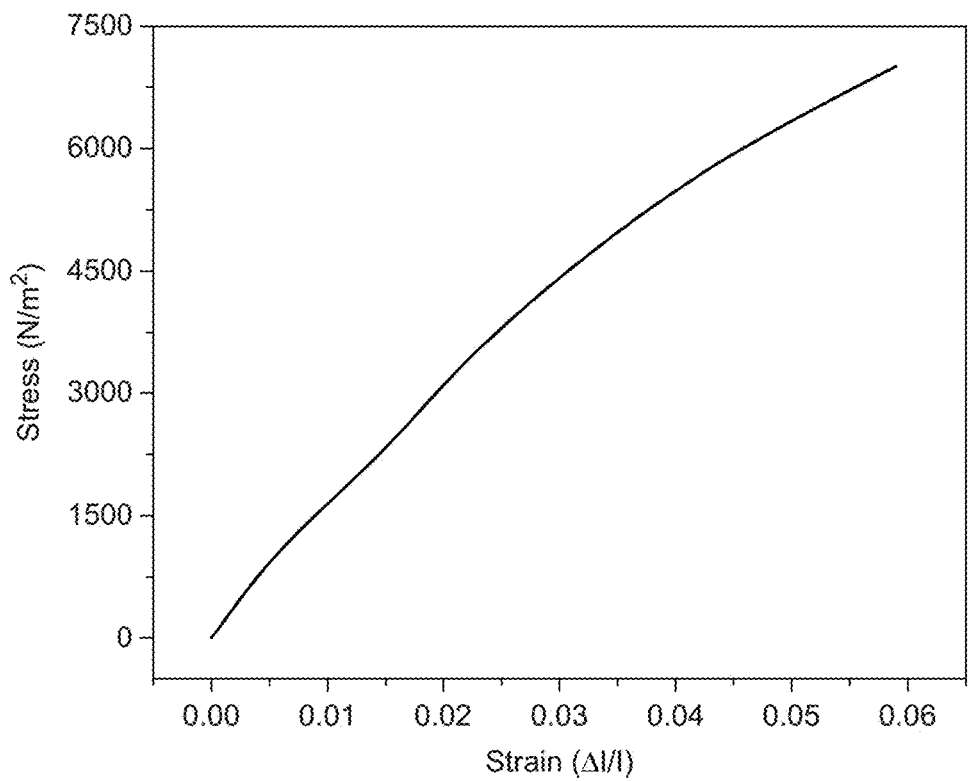
FIG. 8 shows stress-strain relationships of sensors R1 and R2 made of CNT.

FIG. 6 (a) and FIG. 6 (b) show the schematic diagrams of the constant voltage Wheatstone bridge strain sensors without load and with load. As shown it would be evident from comparison of the FIG. 6 (a) and FIG. 6(b) with FIG. 3(b) and FIG. 3(c) that strain sensor R1 and R3 (longitudinal sides of the Wheatstone bridge) are under tension, R2 and R4 (transversal sides of the Wheatstone bridge) are under compression. FIG. 7 shows $\Delta R_1/R_1$ and $\Delta R_2/R_2$ relationships with strain ($\Delta l/l$) under tension and compression and FIG. 8 show stress-strain relationships of sensors R1 and R2 made of CNT, it is seen that this relationship is quasi-linear. The similar relationships were obtained for the strain sensors R3 and R4 made of CNT-Ag$_2$Se (50:50 wt %) composite. For both of CNT based (R1 and R2) sensors the stress-strain behavior was same; likewise both CNT-Ag$_2$Se based strain sensors (R3 and R4) had a similar behavior.

The proper selection of the ingredients of the composite (CNT, Ag$_2$Se and porous rubber) for flexible elastic strain Wheatstone bridge sensors allows to achieve and obtain low temperature coefficient of resistivity ($\gamma=\Delta R/R_o\Delta T$). In the above mentioned relationship for resistivity $\Delta R$, $R_o$ and $\Delta T$ are change of resistance, initial resistance and temperature, respectively.

Resistance-temperature relationships for strain sensors were investigated in the temperature range of 22 to 70° C. and it was found that temperature coefficient of resistances ($\gamma=\Delta R$ 100%/R $\Delta T$) was equal to -0.14%/° C. and -0.08%/° C. for the CNT and CNT-Ag$_2$Se composite, respectively.

Resistance-humidity relationships for strain sensors were investigated in the humidity range of (23-96)% and it was found that humidity coefficient of resistances ($\beta=\Delta R$ 100%/R $\Delta RH$ %) was equal to 0.035 and 0.147 for the CNT and CNT-Ag$_2$Se (50:50 wt %) composite, correspondingly. It was also observed that the increase in the concentration of spherical Ag$_2$Se nanoparticle in the CNT-Ag$_2$Se composite caused to increase initial resistance, while the decrease in the concentration of Ag$_2$Se caused to decrease the initial resistance of composite. The resistance of the single sensors (FIG. 6) fabricated from CNT and CNT-Ag$_2$Se composite at normal condition was equal to 44 k$\Omega$ and 92 k$\Omega$, respectively.

Initially (without of load) when strain is equal to zero, the Wheatstone bridge will be balanced:

$$R1R3=R2R4 \qquad (3)$$

Output of the bridge ($V_o$) will be equal to zero. In this case, it is easier to measure small changes in output voltage ($\Delta V$). Due to some simplification it was shown that:

$$\Delta V=\{(R2/R1)/(1+R2/R1)^2\}\{(\Delta R_1/R_1-\Delta R_2/R_2+\Delta R_3/R_3-\Delta R_4/R_4)\}V_s \qquad (4)$$

Figure 9:
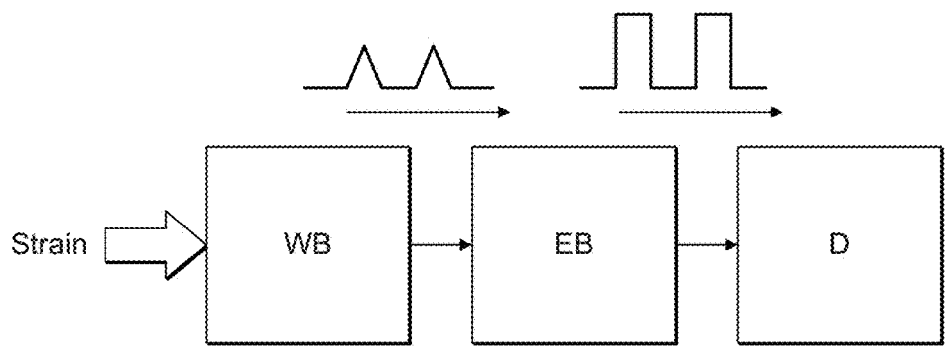
FIG. 9 shows block diagram of the heart rate meter with Wheatstone bridge (WB) strain sensors, electronic block (EB) for counting of pulses and display (D) of electric pulses representing heart beats.

The above equation (Eq. (3)) indicates that the bridge is a linear function of the $\Delta R_1$, $\Delta R_2$, $\Delta R_3$ and $\Delta R_4$—resistance changes. Technologically the balancing of the bridge was achieved by properly changing the each resistor of the bridge. It was done by changing the width of nanomaterial's strip on porous rubber by rubbing in process. If $V_s$ is equal to 10 V, then $\Delta V$ for CNT and CNT-Ag$_2$Se composite based Wheatstone bridge strain sensors will be 0.30-0.35 V. FIG. 9 shows block diagram of the heart rate meter with Wheatstone bridge (WB) strain sensors, electronic block (EB) for counting of pulses and display (D) of electric pulses representing heart beating. Due to the variation of resistances of strain sensors under the effect of heart beating the pulses from output of the Wheatstone bridge are applied to the electronic block, where the pulses are converted into square wave pulses, counted and then applied to the display.

On the basis of experiments the data about the effect of strain, temperature and humidity on the fabricated flexible elastic Wheatstone bridge sensors was obtained. It was found that the Wheatstone bridge is sensitive to strain that allows to use it for the measurement of the heart rate. At the same time the Wheatstone bridge is less sensitive to the effect of temperature and humidity. The reason for this may be the following: under the effect of temperature or humidity the values of all sensors of Wheatstone bridge easily decrease or increase accordingly that will bring to zero output voltage of Wheatstone bridge (FIGS. 6(a) and 6(b)). On the other hand under effect of strain or load (FIGS. 6(a) and 6(b)) two sensors (R1 and R3) are under tension and their resistance increases, but two other sensors (R2 and R4) are under compression and their resistance decreases (FIGS. 6(a) and 6(b)). Therefore sufficiently high voltage is developed as an output of Wheatstone bridge and the bridge can be used for heart rate measurement: under effect of strain to the sensor in output of the Wheatstone bridge (WB) the triangular wave worms are developed that are converted by electronic block (EB) into square wave forms. The number of square wave forms per minute will be shown in digital numbers by display (D) (FIG. 9).

INDUSTRIAL APPLICABILITY

The sensors fabrication is very simple and they show good sensitivity and reliability in operation. As only pristine nanomaterials and porous rubber have been used, so the fabricated sensors are inexpensive from the point of cost of materials. Fabrication technology of the sensors as rubbing in is the simple, economical and reliable. Sensors incorporated in the Wheatstone bridge are sensitive only to the effect of strain; and are not sensitive to temperature and humidity (no interferential effect). Four sensors are incorporated in the Wheatstone bridge; under the effect of strain two sensors undergo tension and the other two undergo compression, resultantly the Wheatstone bridge show high sensitivity. These strain sensors are easy to repair, to recycle and dispose. A heart rate strain sensor can be used in instrumentation for measurement of strain. The strain sensor technology (rubbing in) can be used also for fast selection of different materials for use in the strain sensors as only pristine materials in the form of nanoparticles can be used.

What is claimed is:

1. A Wheatstone bridge for a heart rate meter, comprising:
   a multiwall carbon nanotube powder having a diameter between 10-30 nm;
   a spherical silver selenide nanoparticle of a specific size at 50% wt is added to 50% wt of the multiwall carbon nanotube powder to form a nanocomposite; and
   a porous rubber having a specific length, width and thickness mixed with the nanocomposite to make a porous rubber-CNT-silver selenide strain sensor having a specific length, width and thickness for measuring a heart rate.

2. The strain sensor of claim 1, wherein the specific length, width and thickness of the porous rubber is 50 mm*20 mm*5 mm.

3. The composition of the strain sensor of claim 1, wherein the specific length, width and thickness of the Wheatstone bridge is 20 mm*10 mm*1 mm.

4. The composition of the strain sensor of claim 1, wherein the specific size for the spherical silver selenide nanoparticle is between 0.001 to 100 nm.

5. The composition of the strain sensor of claim 1, wherein the spherical silver selenide nanoparticle is made by combining a silver nitrate solution and sodium selenide solution in a 2:1 ratio.

* * * * *

UNITED STATES PATENT AND TRADEMARK OFFICE
CERTIFICATE OF CORRECTION

| | | |
|---|---|---|
| PATENT NO. | : 9,538,924 B1 | |
| APPLICATION NO. | : 14/860897 | |
| DATED | : January 10, 2017 | |
| INVENTOR(S) | : Abdullah Mohamed Asiri et al. | |

It is certified that error appears in the above-identified patent and that said Letters Patent is hereby corrected as shown below:

On the Title Page
(74) Attorney, Agent, or Firm-  should read Geeta Kadambi; Riddhi IP LLC
instead of (74) Attorney, Agent, or Firm- Greta Kadambi; Riddhi IP LLC Signed and Sealed this
Eighteenth Day of April, 2017

Michelle K. Lee
*Director of the United States Patent and Trademark Office*